US00PP31710P2

(12) United States Plant Patent
Meilland et al.

(10) Patent No.: US PP31,710 P2
(45) Date of Patent: May 5, 2020

(54) BEDDING ROSE PLANT NAMED 'MEITITIKA'

(50) Latin Name: *Rosa hybrida*
Varietal Denomination: MEITITIKA

(71) Applicant: THE CONARD-PYLE COMPANY, West Grove, PA (US)

(72) Inventors: Alain Antoine Meilland, Antibes (FR); William J. Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,711

(22) Filed: Dec. 27, 2018

(51) Int. Cl.
*A01H 5/02* (2018.01)
*A01H 6/74* (2018.01)

(52) U.S. Cl.
USPC ..... Plt./102
CPC ..... *A01H 6/74* (2018.05)

(58) Field of Classification Search
USPC ..... Plt./102
CPC ..... A01H 5/02; A01H 5/0222
See application file for complete search history.

(56) References Cited

U.S. PATENT DOCUMENTS

PP17,391 P2 1/2007 Radler
PP18,562 P2 3/2008 Radler
PP19,032 P2 7/2008 Radler

OTHER PUBLICATIONS https://issuu.com/gardendebut/docs/merged_all_pages_-_final_-_small/40; Jul. 29, 2018; 3 pages.*

* cited by examiner

*Primary Examiner* — Kent L Bell
(74) *Attorney, Agent, or Firm* — Buchanan Ingersoll & Rooney PC

(57) ABSTRACT

A new and distinct variety of bedding rose plant, herein referred to by its cultivar name, 'MEITITIKA', is provided which forms very abundantly on a nearly continuous basis attractive, flat cup shaped flowers that exhibit yellow colored at the beginning of opening to red colored at the end of opening. Attractive, semi-glossy, very dense foliage is formed, which contrasts beautifully with the blossoms. A bushy growth habit is displayed. The disease tolerance is very good, particularly against black spot. The new variety is well suited for providing attractive ornamentation in the landscape.

1 Drawing Sheet

Botanical/commercial classification:
Latin name—*Rosa hybrida.*
Common name—Bedding Rose Plant.
Varietal denomination—'MEITITIKA'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the 'RADBRITE' variety (U.S. Plant Pat. No. 17,391). The male parent (i.e., the pollen parent) was the 'RADSWEET' variety (U.S. Plant Pat. No. 19,032).

The parentage of the new variety can be summarized as follows:

'RADBRITE'×'RADSWEET'

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) forms attractive, flat cup shaped, flowers which are yellow colored at the beginning of the opening to red colored at the end of opening,
(b) forms attractive, very dense, semi-glossy foliage,
(c) exhibits good tolerance to diseases, particularly against black spot, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'RADBRITE' variety (i.e., the seed parent) displays pink colored blossoms and the 'RADSWEET' variety (i.e., the pollen parent) displays light pink colored blossoms, whereas the new variety displays yellow colored blossoms at the beginning of opening that evolve to red colored blossoms at the end of the opening. Moreover, the new variety can be readily distinguished from related similar non-parental varieties. For example, the 'Radsunny' variety (U.S. Plant Pat. No. 18,562) displays yellow colored flower which remain yellow throughout the opening of the flower, whereas the new variety displays yellow colored blossoms at the beginning of opening that evolve to red colored blossoms at the end of the opening.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEITITIKA'.

BRIEF DESCRIPTION OF THE PHOTOGRAPH

The accompanying photograph of FIG. 1 shows as nearly true as it is reasonably possible to make the same, in a color illustration of this character, typical specimens of the plant parts of the new variety. The rose plants of the new variety were approximately two years of age and were observed during June while budded on their own roots and growing outdoors at Le Cannet des Maures, Var, France. Dimensions in centimeters are indicated at the bottom of FIG. 1.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during June while budded on their own roots and growing outdoors at Le Cannet des Maures, Var, France.

Class: Bedding Rose Plant.

Plant:

*Habit*.—Bushy.

*Height*.—Approximately 80 cm on average.

*Width*.—Approximately 80 cm on average.

Branches:

*Color*.—Young stems: commonly near Yellow-Green Group 144A. Adult wood: commonly near Yellow-Green Group 144A.

*Size*.—Length is typically 20 cm to 35 cm on average, diameter is typically 0.6 cm to 0.9 cm on average.

*Internode length*.—Typically 3.0 cm to 6.5 cm on average.

*Thorns*.—Configuration on adult stems: curved downwards on the upper surface and concave on the under surface. Long prickles (≥0.6 cm) — quantity: commonly approximately 11 thorns per 10 cm long young stem and commonly 8 thorns per 10 cm long adult stem. Long prickles (≥0.6 cm) — base shape: oval. Long prickles (≥0.6 cm) — size: commonly near 0.8 cm in length on average on young stems and on adult stems. Long prickles (≥0.6 cm) — color: commonly near Yellow-Green Group 145C on young stems and commonly near Greyed-Orange Group 163C on adult stems. Small prickles (<0.5 cm) — quantity: commonly approximately 27 thorns per 10 cm long young stem and commonly 35 thorns per 10 cm long adult stem. Small prickles (<0.5 cm) — base shape: oval. Small prickles (<0.5 cm) — size: commonly near 0.2 cm in length on average on young stems and on adult stems. Small prickles (<0.5 cm) — color: commonly near Greyed-Purple Group 183D on young stems and commonly near Greyed-Orange Group 164D on adult stems.

Foliage:

*General appearance*.—Very dense with a semi-glossy aspect.

*Number of leaflets*.—3, 5, and 7; most often 5 or 7.

*Terminal leaflet*.—Length: approximately 6.2 cm on average. Width: approximately 3.6 cm on average.

*New foliage*.—Upper surface color: commonly near Yellow-Green Group 146B. Under surface color: commonly near Yellow-Green Group 147C.

*Adult foliage*.—Upper surface color: commonly near Yellow-Green Group 146A. Under surface color: commonly near Yellow-Green Group 147B.

*Entire leaf*.—Length is typically 7.0 cm to 11 cm on average, width is typically 7.0 cm to 9.5 cm on average.

Leaflets:

*Shape*.—Tip: acuminate. Base: obtuse.

*Texture*.—Leathery.

*General appearance*. —Oval.

*Edge*.—Slightly denticulate.

*Serration*.—Small and single.

*Petiole rachis*.—Color of upper surface: commonly near Greyed-Purple Group 182B. Color of under surface: commonly near Yellow-Green Group 147C. Length: typically 2.7 cm to 4.1 cm on average. Diameter: typically 0.1 cm to 0.15 cm on average.

*Petioles*.—Upper surface: no glandular. Under surface: few prickles. Color of upper surface: commonly near Yellow-Green Group 146C. Color of under surface: commonly near Yellow-Green Group 147C. Size: length is typically 2.5 cm to 3.5 cm on average, diameter is typically 1.0 to 1.5 cm on average. Petiole length of terminal leaflet: commonly near 2.4 cm on average. Petiole diameter of terminal leaflet: commonly near 0.1 cm on average.

*Stipules*.—General appearance: adnate, pectinate and rather broad. Length: approximately 1.2 cm on average. Width: approximately 0.6 cm on average. Color of upper surface: commonly near Yellow-Green Group 146B. Color of under surface: commonly near Yellow-Green Group 147C.

Inflorescence:

*Number of flowers per stem*.—Generally between 3 to 7 flowers per stem.

*Bud*.—Shape: conical. Size: small. Length: approximately 1.7 cm on average. Width: approximately 1.6 cm on average. Color as calyx breaks: upper surface: commonly near Yellow Group 9A suffused with near Orange-Red Group 31B. under surface: commonly near Yellow Group 9A.

*Sepals*.—Length: approximately 1.7 cm on average. Width: approximately near 0.5 cm on average. Shape: without extensions at the top: narrow and longish, at the base: upright. Margin: glandular with 0 to 2 very small single extensions. Upper surface: texture: tomentous. color: commonly near Yellow-Green Group 148C. Under surface: texture: smooth. color: commonly near Yellow-Green Group 146C.

*Receptacle*.—Color: commonly near Yellow-Green Group 146C. Length: approximately 0.7 cm on average. Width: approximately 0.4 cm on average. Surface: glandular. Shape: pitcher shaped.

*Peduncle*.—Length: commonly near 3 to 3.5 cm on average. Width: approximately 0.3 cm on average. Surface: glandular. Color: commonly near Yellow-Green Group 146C.

*Flower*.—Average diameter when fully open: commonly between 6.0 to 8.0 cm on average. Depth: typically 3.0 cm to 3.5 cm on average. Borne: commonly between 3 to 7 flowers per stem. Shape: flat cup shaped. Number of petals under normal conditions: approximately 6 to 8 petals on average. Shape of the petal: base: cuneiform. top: rounded. Petal margin: a little ondulated and can be crenated with 1 to 3 crenations. Texture of the petal: leathery. Petal length: approximately 3.4 cm on average. Petal width: approximately 2.9 cm on average. Petal arrangement: imbricated without petaloids. Petal drop: petals drop off cleanly before drying. Fragrance: none. Color when opening: spot at the base: upper surface is commonly near Yellow Group 9B and under surface is commonly near Yellow Group 9C. upper surface of the flower: commonly between near Yellow Group 9B to 9D, suffused with near Red Group 52D. under surface of the flower: commonly between near Yellow Group 9B to 9D, suffused with near Red Group 52D. Color of the open flower: spot at the base: upper surface is commonly near Yellow Group 9B and under surface is commonly near Yellow Group 9C. upper surface of the flower: commonly between near Yellow Group 9D to 11D amply suffused with near between Red Group 52D and 52C. under surface of the flower: commonly between near Yellow Group 9D to 11D amply suffused with near between Red Group 52D and 52C. Anthers: number is approximately 96 on average, length is approximately 0.1 cm on average, coloration is commonly near Yellow-Orange Group 22A, and arrangement is regular around styles. Filaments: length is approximately 0.3 cm on average and coloration is commonly near Orange-Red Group 33B. Styles: length is approximately 0.3 cm on average, coloration is commonly near Red Group 33C, and number is approximately 52 on average. Stigmas: size is approximately 0.1 cm on average and coloration is commonly near Yellow Group 2C. Pollen: not available at this stage. Hips: not available at this stage.

Development:

*Vegetation*.—Strong.

*Blooming*.—Early in the season, very abundant and nearly continuous, typical months the plant blooms is May to October.

*USDA hardiness zone*.—Zone 5.

*Tolerance to disease*.—Very good, and particularly against black spot (*Diplocarpon rosae*).

The new 'MEITITIKA' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of Bedding Rose plant characterized by the following combination of characteristics:

(a) forms attractive, flat cup shaped, flowers which are yellow colored at the beginning of the opening to red colored at the end of opening, (b) forms attractive, very dense, semi-glossy foliage, (c) exhibits good tolerance to diseases, particularly against black spot, and (d) is well suited for providing attractive ornamentation; substantially as herein shown and described.

* * * * *

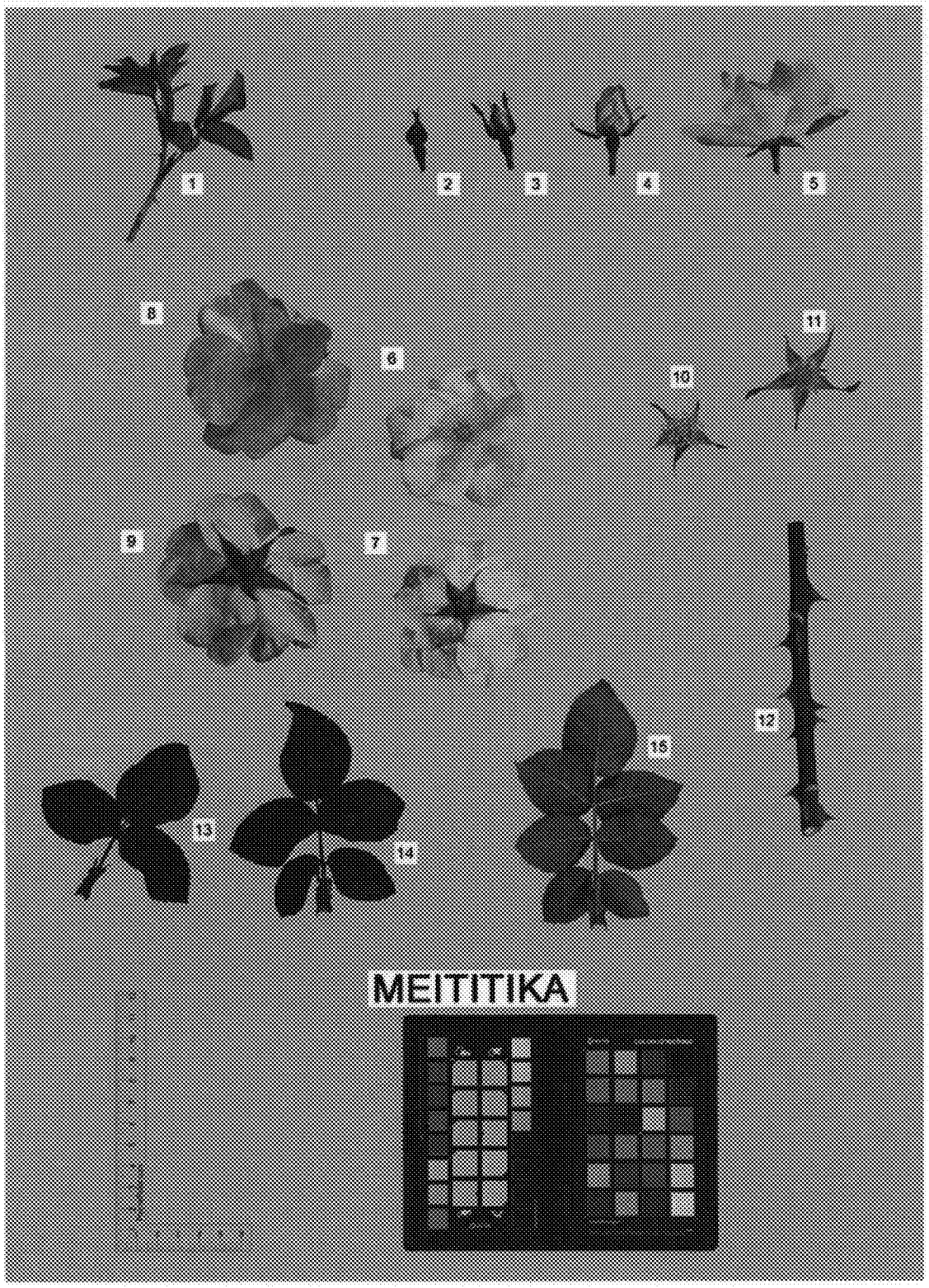
1
2
3
4
5
8
6
10
11
9
7
12
13
14
15
MEITITIKA